United States Patent
Holmer (12)

(10) Patent No.: US 6,559,132 B1
(45) Date of Patent: May 6, 2003

(54) COMPOSITION COMPRISING HEPARIN AS A NON-THROMBOGENIC SURFACE COATING AGENT

(75) Inventor: Erik Holmer, Stockholm (SE)

(73) Assignee: Carmeda AB, Stockholm (SE)

( * ) Notice: Subject to any disclaimer, the term of this patent is extended or adjusted under 35 U.S.C. 154(b) by 0 days.

(21) Appl. No.: 09/763,856

(22) PCT Filed: Sep. 9, 1999

(86) PCT No.: PCT/NO99/00278

§ 371 (c)(1), (2), (4) Date: Feb. 27, 2001

(87) PCT Pub. No.: WO00/13719

PCT Pub. Date: Mar. 16, 2000

(30) Foreign Application Priority Data

Sep. 9, 1998 (NO) .......................................... 19984144

(51) Int. Cl.$^7$ ........................ A61K 31/727; C08B 37/10
(52) U.S. Cl. ........................................ 514/56; 536/21
(58) Field of Search ............................... 514/56; 536/21

(56) References Cited

U.S. PATENT DOCUMENTS 4,446,126 A * 5/1984 Jordan ........................ 424/183

FOREIGN PATENT DOCUMENTS

| EP | 0086187 | 8/1983 |
|---|---|---|
| EP | 0832618 | 4/1998 |

OTHER PUBLICATIONS

"Immobilization of High–Affinity Heparin Oligosaccharides to Radiofrequency Plasma–Modified Polyethylene," Yuan et al.; Journal of Biomedical Materials Research, vol. 27, pp. 811–819; 1993.

"Immobilization of Heparin Oligosaccharides onto Radiofrequency Plasma Modified Pyrolytic Carbon–Coated Graphite," Yuan et al.; Journal of Applied Biomaterials, vol. 6, pp. 259–266; 1995.

* cited by examiner

Primary Examiner—Peter O'Sullivan
(74) Attorney, Agent, or Firm—Nixon & Vanderhye P.C.

(57) ABSTRACT

The present invention relates to a composition comprising heparin to be used as a non-thrombogenic surface when in contact with arterial blood flow. It also relates to a device treated on the surface thereof with such a composition.

9 Claims, 1 Drawing Sheet

COMPOSITION COMPRISING HEPARIN AS A NON-THROMBOGENIC SURFACE COATING AGENT

This application is a 371 of PCT/NO99/00278, filed Sep. 9, 1999.

The present invention relates to a composition comprising heparin to be used as a non-thrombogenic surface coating agent when in contact with arterial blood flow. It also relates to a device treated on the surface thereof with such a composition.

BACKGROUND OF THE INVENTION

Thrombosis is a major health problem in the industrialized world. Thrombosis related diseases cause the death of several millions of people every year and the health care costs have been estimated to be over 90 billion US dollars just for the USA.

There are two different kinds of thrombosis, arterial and venous. As the names suggest the arterial thrombosis occurs in the arteries and the venous thrombosis occurs in the veins. The arterial thrombus is formed at high flow rates and platelets are the main component. Platelets are small cells, diameter around 2 $\mu$m, circulating in the blood. Their main function is to participate in the haemostasis. When platelets are exposed to collagen in damaged or altered vessel walls or in wounds or when exposed to foreign surfaces they adhere to the surfaces, become activated and start to form aggregates. When this occurs in an artery a thrombus with aggregated platelets is formed. The arterial thrombus has also been called the white thrombus because of its appearance which is due to the fact that it mainly contains platelets and very few erythrocytes (red blood cells).

The venous thrombus is formed at low flow rates and the blood coagulation system is the major participant. In plasma a number of proenzymes and effector proteins are present that together constitute the coagulation system. The system can be triggered in several ways and in a cascade-like process one enzyme activates a proenzyme and the formed enzyme activates the next proenzyme. The final enzyme formed is thrombin and that cleaves off two peptides from the plasma protein fibrinogen, which then results in a rapid aggregation of the modified fibrinogen to form a gel, and a fibrin clot or thrombus is formed. The venous thrombus is called the red thrombus because it contains erythrocytes embedded in fibrin.

Diseases related to arterial thrombosis are: myocardial infarction, thrombotic stroke, and peripheral arterial disease. In myocardial infarction a thrombus is formed in one of the coronary arteries and the blood supply to the corresponding part of the heart muscle is stopped or strongly diminished resulting in death of that part of the heart muscle. In thrombotic stroke the blood flow in a cerebral artery is blocked by a thrombus, which usually has been formed somewhere else in the circulation and followed the blood flow to the brain. As the brain is very sensitive to oxygen deprivation, the part of the brain supplied by blood from this artery will be damaged.

Myocardial infarction and thrombotic stroke are very serious conditions with high mortality and therefore, many treatment efforts today intend to prevent them from occurring. The mostly used drug is aspirin (acetylsalicylic acid), which inhibits the activation and aggregation of platelets and thereby prevents the arterial thrombus formation. Large clinical studies have shown that one aspirin a day significantly reduces the risk for having myocardial infarction. For prevention of thrombotic stroke there is also another drug which is commonly used. That is Ticlopedin, which also inhibits platelet aggregation but through somewhat different mechanisms than aspirin.

Diseases related to venous thrombosis are deep venous thrombosis (DVT) and pulmonary embolism. In deep venous thrombosis a thrombus is formed in one of the veins in the extremities usually the legs. That thrombus diminishes the return flow of blood and results in diminished blood supply to that part of the leg or arm. The leg or arm becomes swollen and painful. The condition as such is not life-threatening but if not treated the thrombus can grow and extend and pieces can leave by the return flow and get stuck in the lungs. That condition which is life-threatening is called pulmonary embolism. The clinical practice in dealing with venous thrombosis can be divided into prevention and treatment. However, the drugs used are the same—the difference is in the dosing and time of treatment.

The drugs used are heparin, low molecular weight heparin and dicoumarol derivatives. All of them act as to diminish coagulation and fibrin formation, which is the key process in venous thrombosis. Heparin is a sulfate-containing polysaccharide, which on large scale is isolated from intestinal mucus of swine. It has for many decades been used clinically as an agent for the treatment and prevention of venous thrombosis. Heparin is heterogeneous with a molecular weight from 5,000 to 30,000 daltons and with an average molecular weight of about 12,000–15,000 daltons. Heparin and low molecular weight heparin exert anticoagulant activity by drastically increasing the rate whereby the physiological coagulation inhibitor, antithrombin III (AT), inactivates activated coagulation factors. Only about one third of heparin molecules do bind AT and have a strong anticoagulant activity. This is related to the fact that they contain a specific pentasaccharide sequence with a strong affinity for AT. This fraction of heparin is called the high affinity or HA-fraction. The residual part, the low affinity (LA) fraction, is essentially devoid of anticoagulant activity. Regarding the more important thing, the in vivo antithrombotic activity, the situation is more complex, as not only activation of AT is important but also other mechanisms, such as release of Tissue Factor Pathway Inhibitor (TFPI) contribute to the antithrombotic effect. LA-heparin releases TFPI and thus contributes to the antithrombotic effect of whole heparin despite having no anticoagulant activity.

Heparin also affects platelets but it acts as a weak stimulator of platelet aggregation and it also potentiates the platelet aggregatory action of adenosine diphosphate. There is no difference between the HA- and LA-heparin regarding their ability to affect platelets in this respect as shown by Holmer et al., Thromb Res 1980; 18: 861–69.

Dicoumarol derivatives have antithrombotic action through diminishing synthesis of some coagulation factors in their biologically active forms. That process takes some time and that is why the dicoumarol derivatives cannot be used for immediate antithrombotic treatment.

During the last two decades there has been a large progress in the development of devices for various types of implantation or use in machines, where there is contact with blood. However, that has also created a new type of thrombosis problem. When blood comes into contact with other materials than the fresh natural wall of the blood vessel, activation of the coagulation system starts to occur and thrombotisation can follow. The thromboses formed are of the arterial type with platelets as a dominating element when the foreign surface is subjected to arterial blood flow (Hanson et al. Biomaterials 1982; 519–30). In venous blood flow the situation is mixed with both platelets and coagulation involved.

To prevent thrombosis in devices it is possible to use antiplatelet and antithrombotic drugs. This is not an ideal solution however, as that imposes a bleeding risk and further drug treatment often has to go on for long times which is a disadvantage. That is why far going efforts have been made to find materials of reduced tendency to form thrombosis. Various polymers and plastic materials have been tried. The hydrophilicity/hydrofobicity of the surface has been varied but no break-through composition has been found. As platelets are negatively charged at physiological pH, studies have been performed with surfaces containing negative charges, where it could be expected that the adhesion would be diminished due to the electrostatic repulsion. So far the most successful example of making a surface less thrombogenic through coating of the surface with a negatively charged polymer is to use heparin for the coating to inhibit platelet adhesion. Heparin has the advantage compared to synthetic polymers that it is a physiological compound. It is also the most strongly negatively charged molecule that can be found in the human body. There is no difference between HA- and LA-heparin in this respect.

Different technologies have been developed to attach heparin to surfaces in order to make them less thrombogenic. Ionic binding of heparin to polycationic surfaces has been tried but has been less successful as heparin leached from the surface resulting in loss of antithrombotic properties.

One of the most successful processes for rendering a medical device non-thrombogenic is achieved through covalently binding a heparin fragment to a modified surface of the medical device. The general method and improvements thereof are described in the following European patents: EP-B-0086186, EP-B-0086187 and EP-B-0495820.

These patents describe the preparation of surface modification substrates which are achieved through firstly, a selective cleavage of the heparin polysaccharide chain while aldehyde groups are introduced through an oxidation with nitrous acid. Secondly an introduction of one or more surface modifying layers carrying amino groups on the surface of the medical device, and thereafter the aldehyde groups on the polysaccharide chain are reacted with primary amino groups on surface modifying layers followed by a reduction of the intermediate Schiff's bases to stable secondary amine bonds with for instance cyanoborohydride.

This technology has made it possible to prepare stable and well-defined antithrombogenic surface modifications for medical devices.

There are known many other surface modifications which claim to achieve similar or even better results, such as for instance described in EP-A-0200295 (U.S. Pat. No. 4.600, 652. U.S. Pat. No. 6,642,242.) based on substrates having a layer of a polyurethane urea to which heparin modified to contain aldehyde groups through an oxidation with nitrous acid or periodate, may be bound by covalent links.

Another antithrombogenic surface modification which may be mentioned is described in EP-B-0309473. The surface of the device is modified through the coating with a layer of lysozyme or a derivative thereof to which heparin is adhered.

Yet another surface modification for producing antithrombogenic articles is described in U.S. Pat. No. 4,326,532. In this case, the layered antithrombogenic surface comprises a polymeric substrate, a chitosan bonded to the polymeric substrate and an antithrombogenic agent bonded to the chitosan coating. Japanese Patent Laid-Open No. 04-92673 relates to an antithrombogenic hemofilter also using a chitosan layer for binding heparin. The listing of prior art processes for preparing antithrombogenic surfaces is by no means complete, and it is a clear indication that it is difficult to prepare such coated medical articles which exhibit the properties necessary of successful use in patients, namely stability of the coating, no adverse change of properties of the substrate to be coated and sufficiently high and long lasting antithrombogenic activity.

Thus even if coating of surfaces with heparin has been successful in reducing thrombogenicity there is still need for improvement and the use of a fraction of heparin having optimal properties could be an important step forward.

The present invention describes the preparation and characterization of HA- and LA-heparin, intended for coating of surfaces, as obtained by affinity chromatography on matrix bound AT. It further deals with coating of surfaces of devices with the HA- and LA-heparin preparations. Separation of HA- and LA-fractions of heparin followed by coupling to surface has previously been performed by Yuan et al. (J Biomed Mater Res 1993; 27: 811–20 and J Appl Biomater 1995; 6: 259–66). In the study of Yuan et al. (1995) it was found that the LA-heparin coated surface had higher anticoagulant activity, measured as anti Factor Xa activity, than the HA-heparin coated surface.

In the present invention a surface coated vascular implant (stent) was investigated in an animal experimental thrombosis model. The animal model used was an arterio-venous shunt model in baboons. In that model the blood from one artery passes through a tubing containing the material to be studied and then to a vein. The thromboses formed in this model are of the arterial type and the thrombus formation is followed by measuring the accumulation of radiolabelled platelets.

Contrary to what could be expected from what is known on mechanisms of arterial thrombosis, with its predominant platelet involvement, and what is known about effects of HA- and LA-heparin on platelets, it was found that, when coupled to surface, the HA-fraction was much more efficient that the LA-fraction to prevent formation of arterial thrombosis.

Through the present invention improved non-thrombogenic activity can be obtained and as a result thereof the following advantages can be achieved:

sufficient non-thrombogenicity can be obtained with lower quantities of immobilized heparin. This is especially important for material and devices associated with difficulties to immobilize large amounts of heparin.

higher non-thrombogenicity can be obtained with the same amount of immobilized heparin. This is especially important in applications with strong thrombogenic stimuli e.g. in situations with low blood flow and applications like catheters and vascular grafts with narrow lumen or in cases where the patient otherwise would require additional systemic heparinization.

SUMMARY OF THE INVENTION

One object of the invention is to provide a composition comprising heparin to be used as a non-thrombogenic surface coating when in contact with arterial blood flow. Another object of the invention is to provide a device treated on the surface thereof with such a composition.

DETAILED DESCRIPTION OF THE INVENTION

One object on the invention is to provide a composition comprising heparin enriched with respect to high affinity, HA, heparin, to be coupled to a surface of a medical device, optionally together with a suitable carrier.

Preferably, the composition comprises heparin purified with respect to high affinity, HA, heparin.

The composition according to the invention is optionally combined with a carrier to effect the immobilization of the heparin onto the surface of the medical device.

The carrier is selected from the group of organic compounds carrying functional groups such as amino, aldehydo, hydroxyl, carboxylic acid, carbodiimido or other reactive functional groups that can be bound to functional groups present in or introduced into the heparin.

The functional compounds could be low molecular weight compounds or polymers. Examples of low molecular weight compounds carrying functional groups are tridodecylmethyl-ammonium chloride, benzalkonium chloride derivatives, ethyl dimethylaminopropyl carbodiumide and glutaraldehyde. Examples of polymers are e.g. polyamines such as polyethylenimine (PEI) or polylysine, polycarboxylic acids like polyacrylic acid, polyalcohols like polyvinyl alcohol or polysaccharides and other functional polymers or combinations thereof. The functional groups are present in such an extent that a sufficient amount of HA-heparin can be bound and a strong, antithrombogenic activity can be obtained.

Another object of the invention is to provide a device treated on the surface thereof with a composition according to the invention. A suitable device is selected from but not limited to the group consisting of stents, grafts, stent-grafts, catheters, heart-valves, filters, tubings and membrane containing devices.

Pig mucosal heparin was depolymerized by nitrous acid as described in Larm et al. EP-86186B1. The resulting depolymerized heparin was fractionated by affinity chromatography on matrix bound antithrombin III into its HA- and LA-fractions (Andersson LO et al. Tromb Res 1979; 9: 575–83). As expected the HA-fraction showed very high anticoagulant activity whereas the LA-fraction had very low activity. Two groups of stents of stainless steel (Palmaz-Schatz, PS153, Cordis, Warren, N.J. USA) were then coated (Larrn et al. EP-86186B1) with the two fractions, respectively. Stents are a kind of tublar nets that are used to support the vascular walls and they are used in connection with invasive cardiovascular procedures. Determination of degree of heparin binding showed that essentially the same amounts of the HA-fraction the and LA-fraction, respectively, had been coupled to the surfaces of the two groups of stents. To evaluate the antithrombogenic properties of the two surfaces an establish animal model was used. The model used was an arterio-venous shunt model in baboons. In that model the blood from one artery passes through a tubing containing the material to be studied and then to a vein. The thromboses formed in this model are of the arterial type and the thrombus formation is followed by measuring the accumulation of radiolabelled platelets (Cadroy Y et al. J Lab Clin Med 1989; 113: 436–48).

Stents were placed and expanded in the ex-vivo arterio-venous shunt in a nonanticoagulated baboon that had been injected with radiolabelled platelets. Accumulation of platelets to the stent surface was intermittently monitored by a gamma camera and recorded for a two hour period. Non-coated stents were used as controls. In the control stents platelets immediately started to adhere and continued to accumulate for the duration of the experiment. Stents coated with the LA-heparin fraction showed initially significantly less platelet accumulation than the control but after 40 minutes accumulation started to occur and after two hours there was as much platelet as with the control stents. In contrast no platelet accumulation occurred on the stents coated with the HA-heparin fraction. Even after two hours there was no sign of platelet accumulation. Thus the stents coated with HA-heparin fraction have superior non-thrombogenic properties.

As mentioned above coating of surfaces with heparin has been fairly successful in reducing thrombogenicity. However, there is still need for improvement and as the HA-fraction of heparin seem to be responsible for the main part of the antithrombotic effect it would be an advantage to have a surface enriched with respect to that fraction.

In this study stents have been chosen as the type of device and artificial surface to be investigated. The reason being that the stent is well suited for evaluation in this animal model for arterial thrombosis. However, the type of device whether it is catheters, filters, tubings, vascular grafts or stents is not important for the thrombogenicity of the surface. That is determined by the properties of the surface rather than by the device itself or its bulk material. Thus the conclusions regarding non-thrombogenicity of surfaces reached for the stents are not limited to stents but covers all types of artificial device surfaces in contact with arterial blood.

MATERIALS AND METHODS

Figure 1:
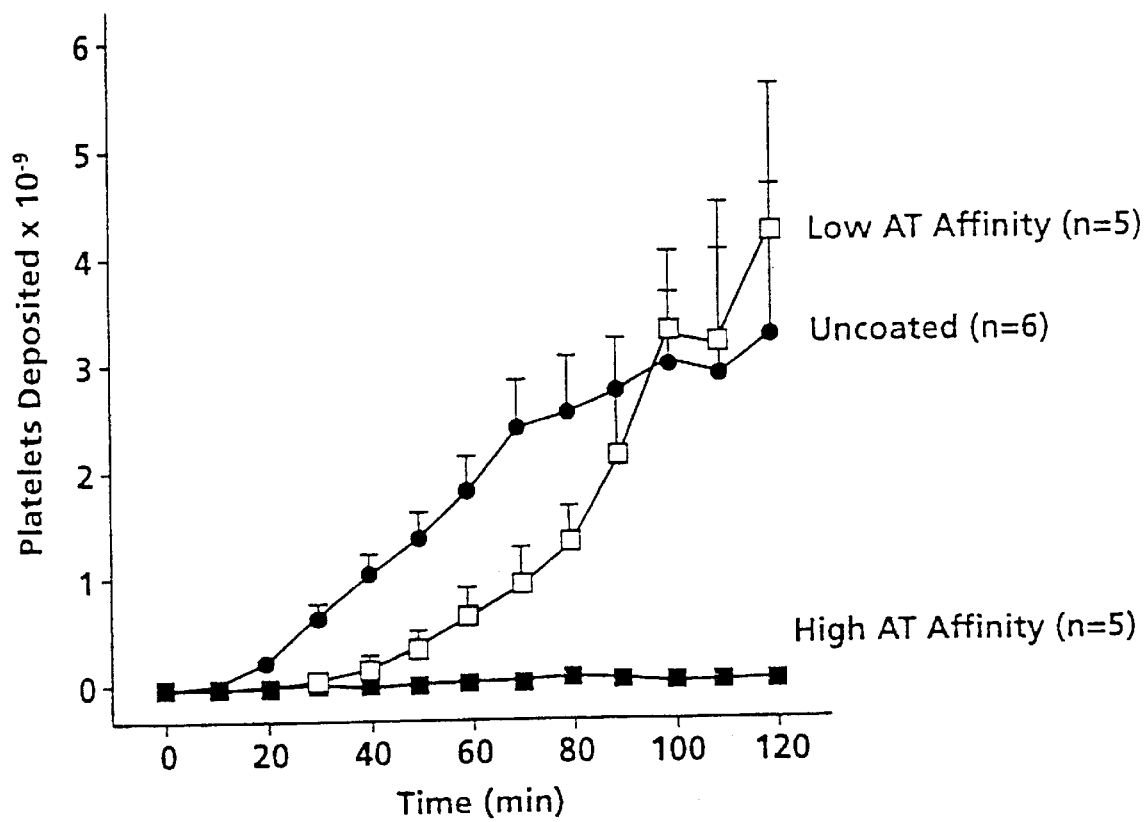
FIG. 1 is a graph showing the adhesion of platelets to stents coated with the HA- and LA-heparin fractions, respectively, and to control stents. Uncoated PS153 stents were used as controls. The numbers in parentheses relate to the number of experiments and animals used in every case.

Pig mucosal heparin was depolymerized by nitrous acid as described in Larm et al. EP-0086186B1. The resulting depolymerized heparin was fractionated by affinity chromatography on matrix bound AT into its HA- and LA-fractions (Andersson LO et al. Tromb Res 1976; 9: 575–83). Human AT was obtained from Pharmacia & Upjohn, Stockholm. Activated CH Sepharose 4B was obtained from Pharmacia Biotech AB, Uppsala, Sweden. Coronary stents, Palmaz-Schatz, PS 153, were supplied by Cordis, Warren, USA. Chromogenic substrates S-2238 and S-2765 were from Chromogenix AB, Mölndal, Sweden. The 4th International Standard for Heparin activity was obtained from the National Institute for Biological Standard and Control, Hertfordshire, United Kingdom.

Preparation of AT-Sepharose was performed according to gel manufacturers instructions. The lyophilized gel (125 g) was reconstituted in buffer and was then reacted with 4 g of AT. The resulting AT-Sepharose (400 ml) had the capacity to bind about 100 mg of HA-heparin. The anticoagulant activities of heparin fractions were determined by a thrombin inhibition assay and by a Factor Xa inhibition assay essentially according the European Pharmacopoeia methods for Low Molecular Mass Heparin using the chromogenic substrates S-2238 and S-2765, respectively. Standard curves were constructed using the 4th International Standard for Heparin and the specific activities were expressed in international units per mg (IU/mg). The heparin content of the heparin subfractions was determined by the carbazole-$H_2SO_4$ method. The amount of heparin bound to the surfaces (heparin density) was determined by a chemical method and expressed as amount of heparin per unit surface area ($\mu g/cm^2$).

The invention is illuminated by the following Examples. These Examples are only illustrative and are not intended to limit the invention in any way whatsoever.

All publications mentioned herein are hereby incorporated by reference. By the expression "comprising" we understand including but not limited to. Thus, other non-mentioned substances or additives may be present.

EXAMPLES

Example 1

Partially nitrous acid depolymerized heparin was separated into its HA- and LA-fractions by affinity chromatography on AT-Sepharose essentially according to Andersson et al. 1976. Heparin loads of 200 mg in 4 ml of 0.15M NaCl were applied to the column and eluted by 500 ml of 0.15M NaCl followed by 500 ml of 2.0M NaCl. The eluate was collected in tubes in 10 ml portions and their heparin content was analyzed by the carbazole method. Tubes containing the LA- and HA-heparin respectively were collected. Each run yielded about 140 mg LA- and 50 mg HA-heparin. The resulting HA- and LA-fractions were characterized with respect to anticoagulant activity. Results are shown in Table 1.

The HA-fraction expressed high anticoagulant activities, 344 IU/mg and 318 IU/mg, in the thrombin- and factor Xa inhibition assays, respectively. The LA-fraction was essentially devoid of activity (<5 IU/mg) by both assays (Table 1).

EXAMPLE 2

Coronary stents were coated with the heparin fractions using technology essentially as previously described (Larm et al. EP-86186B1). Two batches of fifty stents were coated with the HA-fraction and the LA-fraction, respectively. The coated stents were then sterilized using ethylene oxide (EO). The heparin density of the stents is shown in Table 2. The heparin density was essentially the same, about 5 $\mu g/cm^2$, for the two preparations.

The non-thrombogenic properties of the two different heparin coatings on stents were studied in a primate animal experimental model. Stents were placed and expanded in an ex-vivo AV shunt in a non-anticoagulated baboon that had been injected with [1]In radiolabelled platelets. Adhesion of platelets to the stent surface was intermittently monitored by a gamma camera and recorded for a 2 h period. Non-coated PS 153 stents were used as controls. The results are presented in FIG. 1. No platelet adhesion was seen for the HA-stents. In contrast, platelets immediately started to adhere upon implantation of the non-coated control-stent and adhesion continued during the time period studied. The LA-stents showed slightly less adhesion than the control stent up to 1 hour but after 2 hours this difference was abolished and the LA-stent behaved essentially as the control stents.

TABLE 1

Anticoagulant activities of HA- and LA-fractions of partially depolymerized heparin

| Preparation | Recovery % | Activity thrombin inhibition IU/mg | Activity Factor Xa inhibition IU/mg |
| --- | --- | --- | --- |
| HA | 27 | 344 | 318 |
| LA | 67 | <5 | <5 |

TABLE 2

Heparin density on PS153 stents coated with partly depolymerized heparin and its HA- and LA-fractions.

| Preparation | Heparin density $\mu g/cm^2$ |
| --- | --- |
| HA | 4.5 |
| LA | 4.3 |

What is claimed is:

1. A method of use for preparing a non-thrombogenic surface for preventing formation of arterial thrombosis comprising:

using heparin enriched with respect to high affinity, HA, heparin.

2. A method of use for preparing a non-thrombogenic surface for preventing formation of arterial thrombosis comprising:

using heparin enriched with respect to high affinity, HA, heparin, coupled to a surface.

3. A method of use for preparing a non-thrombogenic surface for preventing formation of arterial thrombosis comprising:

using a composition containing heparin enriched with respect to high affinity, HA, heparin, coupled to a surface, together with a suitable carrier.

4. A method of use according to claim 1, wherein the high affinity, HA, heparin is purified.

5. A method of use according to claim 1, wherein the high affinity, HA, heparin is coupled to a surface by end point attachment.

6. A method of use according to claim 3, wherein the carrier is selected from the group of organic compounds having functional groups such as amino, aldehydo, hydroxyl, carboxylic acid, carbodiimido or other reactive functional groups that can be bound to functional groups present in or introduced into the heparin, and wherein the functional compounds can be low molecular weight compounds or polymers.

7. A method of use according to claim 6, wherein the low molecular weight compounds or polymers are selected from the group of tridodecylmethylammonium chloride, benzalkonium chloride derivatives, ethyl dimethylaminopropyl carbodiimide, glutaraldehyde, polyamines, polyethylenimine (PEI), polylysine, polycarboxylic acids, polyacrylic acid, polyalcohols, polyvinyl alcohol, polysaccharides and combinations thereof.

8. A method of use according to claim 1, further comprising:

treating a surface of a device with a composition comprising said heparin enriched with high affinity, HA, heparin.

9. A method of use according to claim 8, wherein the device is selected from the group consisting of stents, grafts, stent-grafts, catheters, heart-valves, filters, tubings and membrane containing devices.

* * * * *